United States Patent
Chen et al.

(10) Patent No.: US 12,173,248 B2
(45) Date of Patent: Dec. 24, 2024

(54) LIQUID MONO-ALKYLATED N-PHENYL-α-NAPHTHYLAMINE COMPOSITIONS AND METHODS OF MANUFACTURING THE SAME

(71) Applicant: LANXESS Corporation, Pittsburgh, PA (US)

(72) Inventors: Huiyuan Chen, Cheshire, CT (US); Cyril Migdal, Pleasant Valley, NY (US); Kevin DiNicola, Wolcott, CT (US); Robert G. Rowland, Woodbridge, CT (US)

(73) Assignee: LANXESS Corporation, Pittsburgh, PA (US)

( * ) Notice: Subject to any disclaimer, the term of this patent is extended or adjusted under 35 U.S.C. 154(b) by 0 days.

(21) Appl. No.: 18/287,748

(22) PCT Filed: Apr. 19, 2022

(86) PCT No.: PCT/US2022/025269
§ 371 (c)(1),
(2) Date: Oct. 20, 2023

(87) PCT Pub. No.: WO2022/225870
PCT Pub. Date: Oct. 27, 2022

(65) Prior Publication Data
US 2024/0209276 A1 Jun. 27, 2024

Related U.S. Application Data

(60) Provisional application No. 63/177,673, filed on Apr. 21, 2021.

(51) Int. Cl.
*C10M 133/12* (2006.01)
*C10N 30/10* (2006.01)

(52) U.S. Cl.
CPC .... *C10M 133/12* (2013.01); *C10M 2215/065* (2013.01); *C10N 2030/10* (2013.01)

(58) Field of Classification Search
CPC .......... C10M 133/12; C10M 2215/065; C10N 2030/10; C09K 15/18; C07C 211/58

USPC .......................................................... 508/563
See application file for complete search history.

(56) References Cited

U.S. PATENT DOCUMENTS

| | | | | |
|---|---|---|---|---|
| 3,414,618 A | | 12/1968 | Randell | |
| 4,770,802 A | * | 9/1988 | Ishida | C10M 133/12 252/401 |
| 5,186,852 A | * | 2/1993 | Ishida | C10M 133/12 252/401 |
| 2008/0045425 A1 | * | 2/2008 | DiBella | C10M 133/12 508/563 |
| 2008/0274925 A1 | * | 11/2008 | Aebli | C08K 5/18 508/563 |
| 2011/0124538 A1 | | 5/2011 | Karseboom et al. | |
| 2019/0127765 A1 | | 10/2019 | Miasnikov | |
| 2021/0269733 A1 | * | 9/2021 | Gatto | C10M 141/06 |
| 2022/0315856 A1 | * | 10/2022 | Michel | C10M 169/04 |

FOREIGN PATENT DOCUMENTS

| | | | | |
|---|---|---|---|---|
| CN | 105777557 A | | 7/2016 | |
| GB | 1552720 A | | 9/1979 | |
| RU | 2 346 029 C2 | | 2/2009 | |
| WO | WO-0123343 A2 | * | 4/2001 | ........... C07C 209/60 |
| WO | 10017029 A2 | | 2/2010 | |

OTHER PUBLICATIONS

International Search Report from corresponding International Application No. PCT/US2022/025269, dated Aug. 2, 2022, three pages.

* cited by examiner

*Primary Examiner* — Ellen M McAvoy
(74) *Attorney, Agent, or Firm* — Nicanor A. Kohncke; Christopher L. McDavid; Ewa M. Wozniak

(57) ABSTRACT

Liquid alkylated N-phenyl-α-naphthylamine (PANA) compositions are disclosed containing a high concentration of mono-alkylated PANA and low levels of di-alkylated and less than 1% by weight of unsubstituted PANA. The novel compositions may be prepared by controlled alkylation of PANA with propylene oligomers followed by subsequent alkylation with at least one second olefin.

24 Claims, No Drawings

LIQUID MONO-ALKYLATED N-PHENYL-α-NAPHTHYLAMINE COMPOSITIONS AND METHODS OF MANUFACTURING THE SAME

Certain alkylated N-phenyl-α-naphthylamines are well known as antioxidants for a variety of fuels and lubricants, such as mineral oils and synthetic oils. For example, N-p-t-octyl-phenyl-α-naphthylamine derived from catalytic alkylation of N-phenyl-α-naphthylamine (PANA) with diisobutylene is a commercially available antioxidant in the form of a crystalline powder. The preparation of p-octylated α- or β-PANA by catalytic alkylation of PANA with diisobutylene is described in U.S. Pat. No. 3,414,618. The product is in solid form, as recrystallization in a solvent is necessary to obtain the product in high purity and as a low dust solid, as further described in International Patent Publication No. WO 2010/017030 A1. Compared to liquid additives, additives in solid form are less desirable, typically requiring additional processing and safety measures in use and suffering from inconvenience and reduced efficiencies with respect to storage and handling.

GB 1,552,720 recognized the advantages of antioxidants in liquid form and disclosed preparing liquid mono p-alkylated PANA compositions by reacting α- or β-PANA with propylene trimer, which is a complex mixture of branched alkene isomers, predominantly branched isomers of nonene, derived from the oligomerization of propylene. Unlike the mono-tertiary alkylated PANA described in U.S. Pat. No. 3,414,618, the nonylated α- or β-PANA disclosed in GB 1,552,720 contained branched nonyl substituents with a variety of configurations, including many asymmetric nonyl groups, which GB 1,552,720 describes as prohibiting crystallization of the product.

U.S. Pat. No. 4,770,802 discloses preparing liquid mono p-alkylated α-PANA compositions by reacting PANA with propylene tetramer and propylene pentamer. The patent describes the resulting alkylated PANA compositions as having a lower tendency to form sludge as compared to PANA alkylated with dimers or trimers of propylene or isobutylene due to improved solubility of the degradation substances formed by oxidation in lubricating oils.

International Patent Publication No. WO 01/23343 A recognized that mono p-alkylated PANA is an useful antioxidant in synthetic ester lubricant, and is also one of two key raw materials for making oligomeric amine antioxidant such as Vanlube® 9317 while di-alkylated PANA cannot. The publication discloses a method of manufacturing alkylated phenylnaphthylamine compositions by alkylating non-alkylated phenylamine with olefin in the presence clay catalyst. Alkylated diphenylamine compositions contain no more than 5% by weight non-alkylated PANA and no more than 5% by weight polyalkylated PANA. In one particular example (example 3), the patent publication describes the preparation of a liquid alkylated PANA containing 2% PANA and >95% mono-nonyl PANA as determined by gas chromatography. A comparative experiment was conducted by repeating the procedure disclosed in the patent publication and the highest assay of mono-nonyl PANA achieved was 91%.

As explained and demonstrated herein, known alkylations of PANA with oligomers of propylene, such as disclosed in U.S. Pat. No. 4,770,802 and GB 1,552,720, result in compositions with considerably lower concentrations of mono-alkylated PANA, higher concentrations of di-alkylated PANA and higher concentrations of residual unreacted PANA, as compared to catalytic alkylation of PANA with diisobutylene. Typically, these known alkylations of PANA with propylene oligomers result in product mixtures containing less than 93% by weight mono-alkylated PANA when using propylene trimers and less than 90% by weight mono alkylated PANA when using propylene tetramers. Correspondingly, more than 4% by weight (often more than 5% by weight) di-alkylated PANA, more than 2% by weight residual unsubstituted PANA when using propylene trimer, and more than 5% by weight residual unsubstituted PANA when using propylene tetramer, based on the total weight of unsubstituted and substituted PANA. In contrast, compositions derived from alkylation of PANA with diisobutylene, disclosed in WO 2010/017030 A, contain ≥95% by weight mono-octyl α-PANA and no more than 2% by weight unsubstituted PANA (often less than 1% by weight).

Unsubstituted PANA has come under increased environmental and safety scrutiny. Further, PANA is a solid, has low solubility in many commonly used base oils, and tends to form sludge when oxidized. There is an unmet need in the industry to produce alkylated α-PANA products in liquid form with reduced levels of unsubstituted PANA. Moreover, in accordance with the present disclosure, it is desirable to also produce alkylated α-PANA compositions in liquid form containing higher proportions of mono-alkylated α-PANA (and lower proportions of di-alkylated α-PANA) compared to the liquid alkylated α-PANA compositions known in the art to increase or maximize antioxidation performance.

The compositions and manufacturing methods of the present disclosure meet these needs, overcoming the above-discussed limitations in the art. In particular, the alkylated N-phenyl-α-naphthylamine composition of the present disclosure contains at least 95% by weight (often more than 97% by weight) of a mixture of mono-alkylated PANA and less than 1% by weight (often less than 0.7% by weight) of unsubstituted PANA, based on the total weight of unsubstituted and substituted PANA in the composition. This higher concentration of mono-alkylated PANA in the composition (i.e., reduced proportions of both unsubstituted PANA and over-alkylated—particularly di-alkylated PANA—in the composition) avoids the undesirable effects of higher unsubstituted PANA concentrations while increasing or maximizing the antioxidant performance of the composition attributed to the reduced proportion of di-alkylated PANA. In addition, the high concentration of desirable mono-alkylated PANA in the presently disclosed composition is similar to the high purity levels of commercially available crystalline mono-p-t-octylated PANA; yet, importantly, the composition of the present disclosure is advantageously a liquid at ambient temperature.

The liquid alkylated PANA compositions of the present disclosure may be prepared as described herein by catalytic alkylation of PANA with two different olefin alkylating materials, namely a mixture of alkene isomers chosen from propylene trimer, propylene tetramer and propylene pentamer, followed by at least one second olefin as described herein, such as diisobutylene and/or α-methylstyrene. The proportion of unsubstituted PANA first alkylated by the propylene oligomers and the extent of residual unsubstituted PANA that is alkylated by the second olefin are controlled such that the resulting alkylated PANA composition contains, based on the total weight of unsubstituted and substituted PANA in the composition, at least 95% by weight of a mixture of mono-alkylated PANA and less than 1% by weight of unsubstituted PANA, and is a liquid at ambient temperature. As detailed further herein, generating in the first alkylation reaction an appropriate amount of PANA alkylated with propylene trimer, tetramer and/or pentamer will stabilize the eventual end product mixture in liquid form without generating undesired high levels of over-alkylated (particularly di-alkylated PANA). In the second alkylation reaction, alkylating the residual unreacted PANA with at least one second olefin as described herein will selectively convert such residual PANA to mono-alkylated PANA, resulting in low levels of both unsubstituted PANA and over-alkylated (particularly di-alkylated) PANA in the product mixture, as desired by the present disclosure.

DETAILED DESCRIPTION

Throughout the present application, "a" or "an" means one or more than one unless indicated otherwise.

For purposes of the present disclosure, "mono-alkylated" PANA refers to mono-alkyl substitution on the phenyl ring of the PANA (i.e., N-alkyl-phenyl-α-naphthylamine).

In one aspect, the present disclosure is directed to an alkylated PANA composition comprising:
at least 95% by weight, e.g., at least 97% by weight or at least 98% by weight, based on the total weight of unsubstituted and substituted PANA in the composition, of a mixture of
(a) an isomeric mixture of mono-alkylated PANA represented by formula I

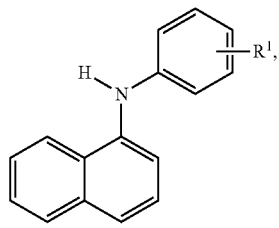

where $R^1$ represents branched alkyl derived from a mixture of alkene isomers chosen from propylene trimer, propylene tetramer and propylene pentamer, and
(b) at least one mono-alkylated PANA represented by formula II

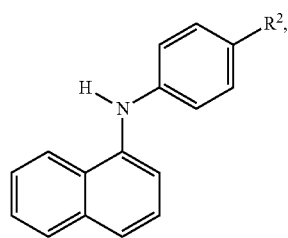

where $R^2$ is a group of formula III not derived from a mixture of alkene isomers chosen from propylene trimer, propylene tetramer and propylene pentamer, or is a group of formula IV,

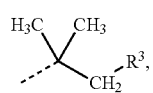

-continued

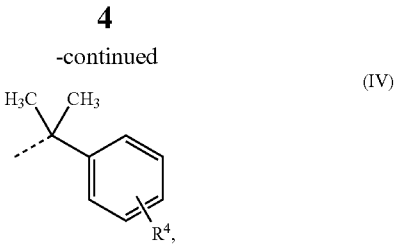

where $R^3$ is a straight-chain or branched $C_{1-12}$ alkyl, (e.g., $C_{1-8}$ alkyl or $C_{1-4}$ alkyl), and
$R^4$ is H or a straight-chain or branched $C_{1-12}$ alkyl, (e.g., $C_{1-8}$ alkyl or $C_{1-4}$ alkyl; and
less than 1% by weight, e.g., less than 0.7% by weight, of unsubstituted PANA, based on the total weight of unsubstituted and substituted PANA in the composition, wherein the composition is a liquid at ambient temperature.

In many embodiments, as much as 97% by weight or higher, based on the total weight of unsubstituted and substituted PANA in the composition, is a mixture of components (a) and (b) above.

Often, unsubstituted PANA is present in the composition at no more than 0.7% by weight, e.g., no more than 0.6% by weight, no more than 0.5% by weight, based on the total weight of unsubstituted and substituted PANA in the composition.

Typically, no more than 4% by weight, e.g., less than 3% by weight, no more than 2% by weight or no more than 1% by weight, based on the total weight of unsubstituted and substituted PANA in the composition, is over-alkylated PANA, particularly di-alkylated PANA.

As described above, component (a) is an isomeric mixture of mono-alkylated PANA represented by formula

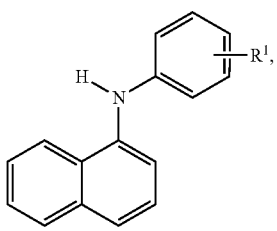

where $R^1$ represents branched alkyl derived from a mixture of alkene isomers chosen from propylene trimer, propylene tetramer and propylene pentamer.

As understood in the art, and as used herein, each of "propylene trimer," "propylene tetramer," and "propylene pentamer" is a complex mixture of branched alkene isomers derived from the oligomerization of propylene. Propylene trimer, tetramer and pentamer are enriched in $C_9$-, $C_{12}$- and $C_{15}$-isomers, respectively. As will be understood in the field, certain amounts of other carbon chain lengths may be present besides the $C_9$ isomers (such as $C_8$ and $C_{10}$) in the case of propylene trimer, besides the $C_{12}$ isomers (such as $C_{11}$ and $C_{13}$) in the case of propylene tetramer, and besides the $C_{15}$ isomers (such as $C_{14}$ and $C_{16}$) in the case of propylene pentamer. Propylene trimer, tetramer and pentamer suitable for the present disclosure are known and commercially available or can be prepared by known oligomerization methods. Often, at least 60% by weight, at least 70% by weight, at least 80% by weight or higher of the propylene oligomers will be $C_9$ isomers (in the case of propylene trimer), $C_{12}$ isomers (in the case of propylene tetramer), or $C_{15}$ isomers (in the case of propylene pentamer).

It is believed that substantially all of $R^1$ in the isomeric mixture of mono-alkylated PANA represented by the formula I (e.g., at least 97%, 98% or more by weight of the isomeric mixture) is in the para-position of the phenyl ring attached to the nitrogen as follows:

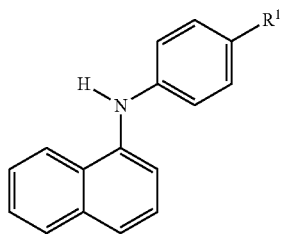

In many embodiments, $R^1$ in formula I represents branched alkyl derived from a mixture of alkene isomers chosen from propylene trimer and propylene tetramer. Often, the mixture of alkene isomers is propylene tetramer.

By itself, component (a), which is an isomeric mixture of mono-alkylated PANA represented by formula I, is a liquid at ambient temperature. This is attributed to the isomeric nature of the branched alkyl substituents in the mixture having a variety of configurations, many of which are asymmetric.

Component (b), as described above, is at least one mono-alkylated N-phenyl-α-naphthylamine represented by formula II

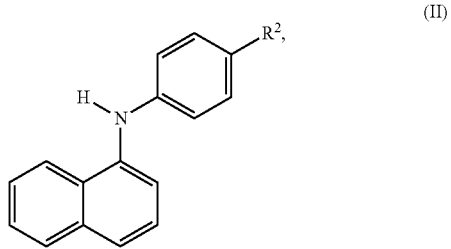

where $R^2$ is a group of formula III not derived from a mixture of alkene isomers chosen from propylene trimer, propylene tetramer and propylene pentamer, or is a group of formula IV,

where $R^3$ is a straight-chain or branched $C_{1-12}$ alkyl, (e.g., $C_{1-8}$ alkyl or $C_{1-4}$ alkyl), and $R^4$ is H or a straight-chain or branched $C_{1-12}$ alkyl, (e.g., $C_{1-8}$ alkyl or $C_{1-4}$ alkyl).

Often, $R^3$ is chosen from methyl, ethyl, n-propyl, isopropyl, n-butyl, sec-butyl, isobutyl or t-butyl. In many embodiments, $R^3$ is t-butyl.

Often, $R^4$ is chosen from H, methyl, ethyl, n-propyl, isopropyl, n-butyl, sec-butyl, isobutyl or t-butyl. In many embodiments, $R^4$ is chosen from H and methyl. Often, $R^4$ is H.

In many embodiments, $R^2$ is chosen from

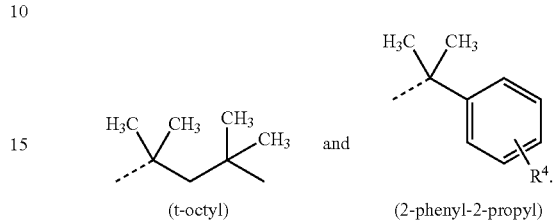

(t-octyl)  (2-phenyl-2-propyl)

For example, $R^2$ is often predominantly t-octyl, i.e., $R^2$ is t-octyl in greater than 50% by weight, such as 60% or more, 70% or more, 80% or more, 90% or more, 95% or more, 98% or more or higher, by weight, of the mono-alkylated PANA of component (b).

By itself, component (b) is typically a solid at ambient temperature.

In certain embodiments, $R^1$ in formula I represents branched alkyl derived from propylene trimer and/or propylene tetramer, and $R^2$ in formula II is chosen from t-octyl and 2-phenyl-2-propyl, such as where $R^2$ is predominantly t-octyl.

The ratio by weight of component (a) to component (b) in the mixture is chosen such that the alkylated PANA composition is a liquid at ambient temperature. For purposes of the present disclosure, "ambient temperature" means a temperature ranging from 20 to 25° C. As used herein in connection with the presently disclosed alkylated PANA composition, the term "liquid" refers to a liquid physical form which remains in liquid form after at least 30 days of storage at ambient temperature. Typically, the alkylated PANA composition of the present disclosure remains in liquid form at ambient temperature for not less than 60 days, often not less than 90 days, such as not less than 180 days, not less than 270 days or not less than two years. Typically, the alkylated PANA composition remains in liquid form over a wide temperature range, for example, as low as 10° C., 5° C., 0° C. or lower, such as from 0° C., from 5° C. or from 10° C. to 60° C.

The ratio by weight of the component (b) to the component (a) in the alkylated PANA composition of the present disclosure may be tuned to optimize the liquid properties and performance (particularly oxidation control) of the composition. For example, the ratio may be optimized to achieve a desired liquid composition while maintaining or maximizing a high nitrogen content (N % by weight) in the alkylated PANA composition for optimal oxidation control. In general, an optimized ratio of the component (b) to the component (a) in the composition depends on the particular chemistries of the formulas I and II. Typically, component (b) constitutes no more than a small majority by weight relative to component (a). In many embodiments, the proportion by weight of component (b) is about equal to or is less than the proportion by weight of component (a) in the mixture. For example, in many embodiments, the ratio by weight of the mono-alkylated PANA represented by formula II (i.e., component (b)) to the isomeric mixture of mono-alkylated PANA represented by formula I (i.e., component (a)) is from about 1.2:1 to about 0.15:1, for example, from about 1:1 to about 0.15:1, such as from about 1:1 to about 0.25:1, from about 0.85:1 to about 0.25:1 or from about 0.7:1 to about 0.4:1.

In certain embodiments, $R^1$ in formula I represents branched alkyl derived from propylene tetramer, $R^2$ in formula II is chosen from t-octyl and and 2-phenyl-2-propyl (e.g., $R^2$ is t-octyl), and the ratio by weight of the mono-alkylated PANA represented by formula II (i.e., component (b)) to the isomeric mixture of mono-alkylated PANA represented by formula I (i.e., component (a)) is from about 0.85:1 to about 0.25:1, such as from about 0.7:1 to about 0.4:1.

The alkylated PANA compositions of the present disclosure typically have a kinematic viscosity according to ASTM D 445 of less than 60 cSt at 100° C., in particular often less than 50 cSt, less than 40 cSt or less than 30 cSt at 100° C.

Also disclosed herein are processes for producing the alkylated PANA composition of the present disclosure.

In one aspect, a process for producing an alkylated PANA composition comprises:
  (i) reacting a reaction mixture comprising unsubstituted PANA, a mixture of alkene isomers chosen from propylene trimer, propylene tetramer and propylene pentamer, and an acidic alkylation catalyst to form an intermediate reaction mixture comprising an isomeric mixture of mono-alkylated PANA and residual unsubstituted PANA, and
  (ii) adding at least one second olefin chosen from olefins of formulas Va, Vb, and VI

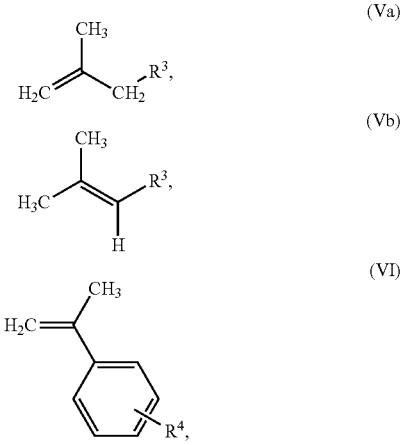

where $R^3$ is a straight-chain or branched $C_{1-12}$ alkyl, (e.g., $C_{1-8}$ alkyl or $C_{1-4}$ alkyl), and $R^4$ is H or a straight-chain or branched $C_{1-12}$ alkyl, (e.g., $C_{1-8}$ alkyl or $C_{1-4}$ alkyl), to the intermediate reaction mixture and reacting the intermediate reaction mixture in the presence of an acidic alkylation catalyst to produce an alkylated PANA composition, wherein the proportion of unsubstituted PANA in the reaction mixture that is alkylated by the mixture of alkene isomers in step (i) and the extent of residual unsubstituted PANA that is alkylated by the second olefin in step (ii) are controlled such that the resulting alkylated PANA composition:
  (1) contains at least 95% by weight, e.g., at least 97% by weight or at least 98% by weight, of a mixture of mono-alkylated PANA, based on the total weight of unsubstituted and substituted PANA in the composition, and
  (2) contains less than 1% by weight, e.g., less than 0.7% by weight or less than 0.5% by weight, of unsubstituted PANA, based on the total weight of unsubstituted and substituted PANA in the composition, and
  (3) is a liquid at ambient temperature.

As described above, in many embodiments, as much as 97% by weight, 98% by weight, or higher of the resulting alkylated PANA composition, based on the total weight of unsubstituted and substituted PANA in the composition, is a mixture of mono-alkylated PANA.

Often, unsubstituted PANA is present in the resulting composition at no more than 1% by weight, e.g., no more than 0.7% by weight, no more than 0.6% by weight or no more than 0.5% by weight, based on the total weight of unsubstituted and substituted PANA in the composition.

Typically, no more than 4% by weight, e.g., less than 3% by weight, no more than 2% by weight of the resulting composition, based on the total weight of unsubstituted and substituted PANA in the composition, is over-alkylated PANAs, particularly di-alkylated PANAs.

The alkylation reactions of steps (i) and (ii) above are Friedel-Crafts type reactions catalyzed by an acidic catalyst. The acidic alkylation catalysts used in steps (i) and (ii) need not be, but are often, the same. The present disclosure is not limited to any particular type of acidic alkylation catalyst and a wide variety of such catalysts for Friedel-Crafts type reactions are known in the art, including mixtures of such catalysts. For example, suitable catalysts include acid clays and metal halides, such as $AlCl_3$, $ZnCl_2$, $FeCl_3$, $SnCl_4$, $TiCl_3$ and the like. Preferably, the process uses an acid clay catalyst. Acid clay catalysts are expected to preferentially facilitate the formation of mono-alkylated PANA with further advantages of producing a low colored product and easy removal Preferably, the acid clay catalyst is an acid activated montmorillonite.

Examples of suitable acid clays include acid activated clays based on bentonite, such as F-20X, F-24X, and F-25X from EP Engineered Clays, and Tonsil® from Clariant, and acid activated phyllosilicates, for example those commercially available under the name Fulcat® from BYK division of ALTANA, such as Fulcat®-22 B, -22F, and -435.

In step (i), a reaction mixture comprising unsubstituted PANA, a mixture of alkene isomers chosen from propylene trimer, propylene tetramer and propylene pentamer, and an acidic alkylation catalyst is reacted to form an intermediate reaction mixture comprising an isomeric mixture of mono-alkylated PANAs and residual unsubstituted PANA. The mixture of alkene isomers in the reaction mixture may be propylene trimer, propylene tetramer, propylene pentamer or any combination thereof, as described herein. In many embodiments, the mixture of alkene isomers is chosen from propylene trimer and propylene tetramer. Often, the mixture of alkene isomers is propylene tetramer.

The isomeric mixture of mono-alkylated PANA formed in the intermediate reaction mixture is represented by formula I, as described herein for component (a). As described in more detail below, only a portion of the unsubstituted PANA in the reaction mixture of step (i) is alkylated by the propylene trimer, propylene tetramer and/or propylene pentamer, hence an amount of residual unsubstituted PANA remains in the intermediate reaction mixture formed from the alkylation in step (i).

In step (ii), the at least one second olefin is added to the intermediate reaction mixture and the intermediate reaction mixture is reacted in the presence of an acidic alkylation catalyst to produce an alkylated PANA composition. The at least one second olefin is chosen from those of the formulas Va, Vb and VI

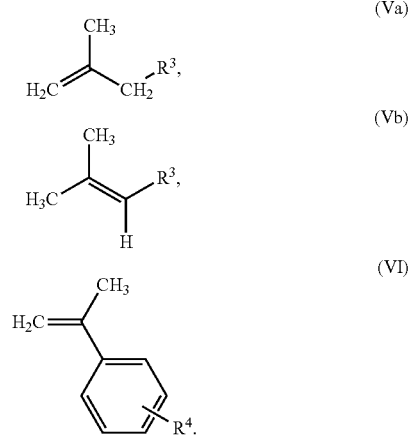

$R^3$ and $R^4$ correspond to $R^3$ and $R^4$ in the formulas III and IV above. Olefins of the formulas Va, Vb and VI are known and commercially available and/or can be prepared by known methods.

Often, the at least one second olefin is diisobutylene, α-methylstyrene or any combination thereof. In many embodiments, the second olefin is diisobutylene. For example, often, at least 50% by weight, such as 60% or more, 70% or more, 80% or more, 90% or more, 95% or more, 98% or more or higher, by weight, of the second olefin is diisobutylene. In many embodiments, the second olefin is diisobutylene.

In some embodiments, the mixture of alkene isomers is propylene trimer and/or propylene tetramer, and the at least one second olefin is diisobutylene.

Excess propylene oligomer present in the intermediate reaction mixture from the first alkylation reaction is often removed (such as by stripping or distillation, often under vacuum) from the intermediate reaction mixture before adding the at least one second olefin and may be recycled for re-use in the process. Alternatively, as the at least one second olefin is more reactive than the mixture of alkene isomers chosen from propylene trimer, propylene tetramer and propylene pentamer, the process may be carried out without removing the excess propylene oligomers from the intermediate reaction mixture before adding the second olefin.

Additional acid catalyst may be added to the intermediate reaction mixture for catalyzing the alkylation in step (ii). The acid catalyst from step (i) may, but need not be, removed (such as by filtration) from the intermediate reaction mixture before adding the at least one second olefin. If the catalyst from step (i) is removed from the intermediate reaction mixture prior to adding the second olefin, additional acid catalyst is added to the intermediate reaction mixture to catalyze the alkylation in step (ii). The acid catalyst may be recycled for re-use in the process.

In step (ii), at least one second olefin chosen from olefins of the formulas Va, Vb, and VI efficiently and selectively reacts with the residual unsubstituted PANA in the intermediate reaction mixture, forming the mono-alkylated PANA represented by formula II, as described herein for component (b).

Importantly, the proportion of unsubstituted PANA in the reaction mixture that is alkylated by the mixture of alkene isomers in step (i) and the extent of residual unsubstituted PANA that is alkylated by the at least one second olefin in step (ii) are controlled such that the resulting alkylated PANA composition:

(1) contains at least 95% by weight, e.g., at least 97% by weight or at least 98% by weight, based on the total weight of unsubstituted and substituted PANA in the composition, of a mixture of mono-alkylated PANA (i.e., a mixture of component (a) and component (b) described above), and (2) contains less than 1% by weight, e.g., less than 0.7% by weight or less than 0.5% by weight, based on the total weight of unsubstituted and substituted PANA in the composition, of unsubstituted PANA, and (3) is a liquid at ambient temperature.

In particular, in step (i), the proportion of unsubstituted PANA in the reaction mixture that is alkylated by the mixture of alkene isomers is controlled to ensure that the eventual end alkylated PANA composition will be a liquid at ambient temperature and to limit the formation of over-alkylated-particularly di-alkylated-PANA, which formation is found to occur typically in the latter stages of the alkylation of PANA with propylene oligomer(s) as the PANA is increasingly converted. In this regard, a large enough proportion of unsubstituted PANA in the reaction mixture is alkylated by the mixture of alkene isomers to ensure that the end alkylated PANA composition—formed after subsequent alkylation with the at least one second olefin in step (ii)—will be a liquid at ambient temperature. But the proportion of unsubstituted PANA alkylated by the propylene oligomer(s) is not so high as to result in the formation of di-alkylated PANA that would cause the end product-formed after subsequent alkylation with the second olefin in step (ii)—to have less than 95% by weight of mono-alkylated PANA.

In step (ii), the residual unsubstituted PANA in the intermediate reaction mixture is alkylated by the at least one second olefin such that the concentration of unsubstituted PANA in the resulting alkylated PANA composition is less than 1% by weight, e.g., less than 0.7% by weight or less than 0.5% by weight, based on the total weight of substituted and unsubstituted PANA in the end composition.

Often at least 40%, such as at least 45%, at least 50% or at least 55%, but no more than 85%, often no more than 80%, such as no more than 75% or no more than 70%, of the unsubstituted PANA in the reaction mixture is alkylated by the mixture of alkene isomers chosen from propylene trimer, propylene tetramer and propylene pentamer. In certain embodiments, the mixture of alkene isomers is propylene trimer, and the proportion of unsubstituted PANA in the reaction mixture alkylated by the propylene trimer is at least 40%, such as at least 45%, at least 50% or at least 55%, but no more than 85%, e.g., no more than 80% or no more than 75%. In certain embodiments, the mixture of alkene isomers is propylene tetramer, and the proportion of unsubstituted PANA in the reaction mixture alkylated by the propylene tetramer is at least 40%, such as at least 45%, at least 50% or at least 55%, but no more than 80%, e.g., no more than 75% or no more than 70%.

Precise lower and upper boundaries of the proportion of unsubstituted PANA that can be alkylated by the propylene oligomer(s) and still (in the case of the upper boundary)

sufficiently limit the formation of di-alkylated PANA and (in the case of the lower boundary) ensure a liquid end product will vary depending on the identity of the particular mixture of alkene isomers and the at least one second olefin used in the alkylation reactions (such olefins dictating the particular chemistry of the produced isomeric mixture of mono-alkylated PANA of formula I and mono-alkylated PANA of formula II herein), as well as on the type of catalyst and the reaction conditions, such as reaction temperature.

In general, the reaction conditions, e.g., temperature, pressure, concentrations of reaction components, and the like are similar to those used in other similar Friedel-Crafts reactions known in the art. Examples of suitable reaction conditions include, but are not limited to, those described below.

Often, the molar ratio of the mixture of alkene isomers chosen from propylene trimer, propylene tetramer and propylene pentamer to the unsubstituted PANA to be alkylated in step (i) ranges from about 2.5:1 to about 3.5:1, often from about 2.8:1 to about 3.2:1. Often, the weight ratio of the acidic alkylation catalyst to the unsubstituted PANA to be alkylated in step (i) ranges from about 0.2:1 to about 1:1, often from about 0.4:1 to about 0.8:1.

Suitable reaction temperatures for the alkylation reaction of unsubstituted PANA with the mixture of alkene isomers in step (i) often range from about 100 to about 200° C., often from about 130 to about 160° C.

The process is not limited to any particular technique for preparing the reaction mixture. Reaction components may be added as a single amount or in multiple additions, metered into the reaction mixture at constant or varying rates, or by another method of addition.

The reaction of the unsubstituted PANA with the mixture of alkene isomers chosen from propylene trimer, propylene tetramer and propylene pentamer is allowed to proceed until the targeted proportion of unsubstituted PANA has been alkylated, as discussed above.

In the alkylation reaction of step (ii), often the molar ratio of the at least one second olefin to the residual unsubstituted PANA in the intermediate reaction mixture ranges from about 2:1 to about 7:1, often from about 3:1 to about 5:1. The process is not limited to any particular technique for adding the at least one second olefin to the intermediate reaction mixture. The second olefin may be added as a single amount or in multiple additions, metered into the intermediate reaction mixture at constant or varying rates, or by another method of addition.

Often, the ratio by weight of the acidic alkylation catalyst to the residual unsubstituted PANA in the intermediate reaction mixture ranges from about 0.4:1 to about 1:1, often from about 0.6:1 to about 0.8:1.

Suitable reaction temperatures for the alkylation reaction of the residual unsubstituted PANA with the at least one second olefin in step (ii) often range from about 100 to about 160° C., often from about 110 to about 140° C.

The reaction of the residual unsubstituted PANA in the intermediate reaction mixture with the second olefin is allowed to proceed until the unsubstituted PANA concentration in the product is less than 1% by weight, e.g., less than 0.7% by weight or less than 0.5% by weight, based on the total weight of substituted and unsubstituted PANA in the product.

The alkylation reactions of the present disclosure are not limited to any particular type of reaction vessel and may be run in an open reaction vessel, e.g., under reflux conditions, or under pressure in a sealed reaction vessel, often with a pressure less than 60 psig, e.g., less than 40 psig or less than 20 psig. The reactions may be run in the presence of an added organic solvent but are often run in the absence of an added solvent.

As discussed above for the ratio by weight of components (b) and (a) in the alkylated PANA composition, the proportion of the unsubstituted PANA alkylated by the propylene oligomer(s) relative to the proportion of residual unsubstituted PANA alkylated by the at least one second olefin may be tuned to optimize the liquid properties and performance (particularly oxidation control) of the composition. For example, for a given reaction system of particular propylene oligomer(s), catalyst and second olefin, the above described proportions may be optimized to achieve a desired liquid composition while maintaining or maximizing a high nitrogen content (N wt %) in the resulting alkylated PANA composition for optimal oxidation control.

The acidic alkylation catalyst can be removed from the alkylated PANA composition by filtration or other known separation methods. Unreacted olefins (and olefin byproducts) may be removed from the alkylated PANA composition by known techniques, such as by stripping or distillation, often under vacuum. The unreacted propylene oligomer(s) and second olefin may be recycled for re-use in the process.

The alkylated PANA compositions of the present disclosure are useful as antioxidants, such as for lubricants and polymers. In particular, the alkylated PANA compositions provide excellent antioxidant activity in lubricants, such as in industrial, marine, aviation, automotive and grease applications, in particular, such as in motor, engine, turbine, chain, gear, hydraulic, compressor and other lubricating oils and fluids, as well as in industrial and automotive grease applications.

In one embodiment, a lubricating oil composition comprises (A) a lubricating oil and (B) an alkylated PANA composition of the present disclosure in an amount effective to provide antioxidative activity. The lubricating oil may be any lubricating oil, natural, synthetic or mixtures thereof, of lubricating viscosity suitable for the intended application, and a wide range of lubricating oils is known in the art. In many embodiments, the lubricating oil is a majority component, i.e., present in more than 50% by weight based on the weight of the lubricating oil composition, for example, 60% by weight or more, 70% by weight or more, 80% by weight or more, 90% by weight or more, 95% by weight or more or 98% by weight or more.

In many embodiments, the presently disclosed alkylated PANA compositions are present in the lubricating oil composition at from about 0.1 to about 10% by weight, based on the total weight of the lubricating oil composition, often from about 0.2 to about 5% by weight, from about 0.2 to about 3% by weight or from about 0.5 to 2% by weight.

The lubricating oil composition may include any number of other additives commonly used in such compositions, such as dispersants, detergents, corrosion/rust inhibitors, other antioxidants, anti-wear agents, anti-foamants, friction modifiers, seal swell agents, emulsifiers, VI improvers, pour point depressants, and others. The types and uses of these additives are known, such as described in US Patent Publication No. 2019/01277656, which is incorporated herein by reference for its disclosure of such additional additives useful in the formulation of lubricating oil compositions.

In general, the lubricating oil compositions typically contain additives in a collective concentration ranging from about 0.2 to about 30% by weight, e.g., from about 0.2 to about 20% by weight, from about 0.2 to about 15% by weight, from about 0.5 to about 10% by weight, or from about 0.5 to about 5% by weight.

EXAMPLES

Analytical Procedures
Gas Chromatography:

Product compositions and the compositions of reaction mixtures that were taken from the reactor during the reaction proceedings were analyzed by capillary column gas chromatography to determine their chemical composition. The weight percentages shown in the Tables below for the unsubstituted and alkylated PANA components are based on the total weight of unsubstituted and substituted PANA in the respective compositions.

Instrument: Agilent 7890 or Hewlett Packard 6890
Injector Technique: Cool on Column
Injection Volume: 0.5 μl
Column: DB 5MS or equivalent, 15 m, 0.53 mm
Detector: FID
Integration: 1.5 to 27 min
Carrier Gas: He (6.0 ml/min)
Auxiliary gases: $H_2$ (40 ml/min); Air (400 ml/min)

Temperature
Injector: 3 min at 50° C., 50° C./min up to 290° C., 19.2 min at 290° C.
Oven: 1 min at 40° C., 25° C./min up to 200° C.; 10° C./min up to 320° C., 7.6 min at 320° C.
Detector: 330° C.
Duration: 27 min
Sample preparation: 50 mg in 5 ml acetone Nitrogen Content:
Nitrogen content (% by weight) was determined by elemental analysis according to the Dumas method.

Physical Analysis:
Kinetic viscosity was determined according to the Ubbelohde method at the stated temperature of 100° C.

Performance Tests
Resistance to oil oxidation was measured per ASTM D2272 rotating pressure vessel oxidation test (RPVOT) at 150° C. Oxidation induction time was reported in minutes. Resistance to oil oxidation was also measured per ASTM D6186 pressure scanning differential calorimetry (PDSC) at 195° C. Oxidation induction time was reported in minutes.

Comparative Example 1

The product composition of a high assay N-p-t-octyl-phenyl-α-naphthylamine commercially available as a powder under the name Irganox® L06 was determined by gas chromatography and the results are shown in Table 1 (see Comp1).

Comparative Example 2

The product composition of an alkylated PANA composition commercially available as a liquid under the name Naugalube® APAN was determined by gas chromatography and the results are shown in Table 1 (see Comp2). Naugalube® APAN is derived from the known alkylation of PANA with propylene tetramer.

Comparative Example 3 (with Reference to Example 3 of Patent Publication No. WO 01/23343 A with a Scaleup Factor of 2)

A Parr reactor was charged with 45.1 grams of N-phenyl-1-naphthylamine and 9.7 grams of F-20X (from EP Engineered Clays), and the reactor was pressurized with $N_2$ at 50 psig and vented three time. The reactor was heated to 55° C. at which point agitation was turned on. The reactor continued to be heated until the temperature of about 105° C. The reactor was vented and then closed. 132.1 grams of propylene trimer (imperial oil, Sarnia, Ontario CA) were added to the reactor over 30 minutes while the reactor temperature was increased to 150° C. over 15 minutes and held at the temperature of 150° C. for additional 15 minutes. Upon the completion of propylene trimer addition, the reactor temperature was set at 142° C. and held at 142° C. for 4 hours. After completion of the reaction, the acid clay was removed by filtration and the resulting filtrate was heated under gradually reduced pressure to remove unreacted propylene trimer. The final distillation temperature was at 170° C. and the vacuum was 2 mm Hg. A transparent, light yellow, viscous liquid (66.5 g) was obtained without further purification. About 91 grams distillate was collected in the receiver. The distillate's gas chromatography composition indicated that there was no PANA detected. Viscous liquid's composition was determined by gas chromatography and the results are shown in Table 1 (see Comp3).

Examples 1 to 4—General Synthesis Method

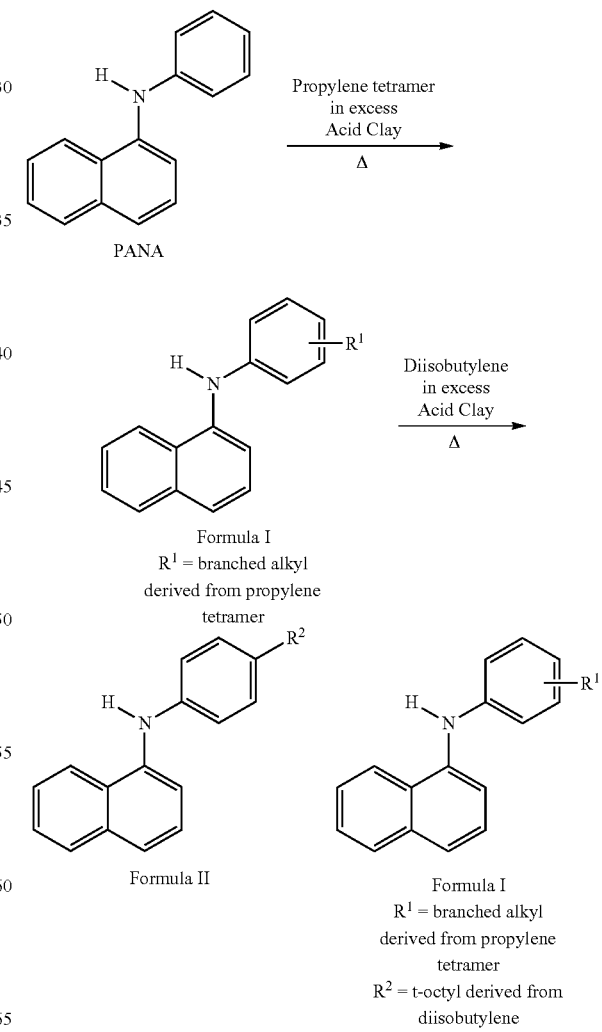

Example 1

A Parr reactor was charged with 80.1 g (0.37 moles) phenyl-α-naphthylamine (PANA), 40.1 g acid clay F-20X (EP Engineered Clays) and 50.5 g (0.30 moles) propylene tetramer at ambient temperature. The reactor was sealed and then heated with stirring to 145° C. 32.0 g (0.19 moles) propylene tetramer were added to the reactor over three hours at 145° C. The reaction was held at 145° C. until 55% of the PANA was converted. PANA conversion was determined by GC composition analysis of in-process samples taken at given intervals of time.

The reactor was then cooled to 120° C. The pressure was released and the reactor was connected with a distillation head, condenser, receiver and vacuum/$N_2$ manifold. With stirring, vacuum was applied to the reactor and the pressure was gradually reduced to 20 torr. Unreacted propylene tetramer was removed by vacuum distillation (about 90 minutes).

Vacuum was released with $N_2$, the reactor was disconnected from the distillation column, and 66.6 grams (0.59 moles) of diisobutylene was added to the reactor. The reactor was resealed and maintained at 120° C. for 1.3 hours. An additional 9.0 g (0.08 mole) diisobutylene was added to the reactor over about 45 minutes at 120° C. The reaction was held at 120° C. until PANA conversion was greater than 99%.

After completion of the reaction, the acid clay was removed by filtration and the resulting filtrate was distilled under reduced pressure to remove unreacted olefins. A transparent, yellow, viscous liquid (101.6 g) was obtained without further purification.

The product composition was determined by gas chromatography and the results are shown in Table 1. Samples of the product mixture were observed at ambient temperature and at 0 to 5° C. for over three months and remained in liquid form.

Example 2

A Parr reactor was charged with 75.2 g (0.34 moles) phenyl-α-naphthylamine (PANA), 37.6 g acid clay F-20X (EP Engineered Clays) and 49.5 g (0.30 moles) propylene tetramer at ambient temperature. The reactor was sealed and then heated with stirring to 145° C. 47.1 g (0.28 moles) propylene tetramer were added to the reactor over 2.7 hours at 145° C. The reaction was held at 145° C. until 67% of the PANA was converted.

The reactor was then cooled to 120° C. The pressure was released and the reactor was connected with a distillation head, condenser, receiver and vacuum/$N_2$ manifold. With stirring, vacuum was applied to the reactor and the pressure was gradually reduced to 20 torr. Unreacted propylene tetramer was removed by vacuum distillation (about 90 minutes).

Vacuum was released with $N_2$, the reactor was disconnected from the distillation column, and 65.8 grams (0.59 moles) of diisobutylene was added to the reactor. The reactor was resealed and maintained at 120° C. for 1.5 hours. An additional 16.0 g (0.14 mole) diisobutylene was added to the reactor over about 1.2 hours at a temperature between 100 and 120° C. The reaction was held at 100° C. until PANA conversion was greater than 99%.

After completion of the reaction, the acid clay was removed by filtration and the resulting filtrate was distilled under reduced pressure to remove unreacted olefins. A transparent, yellow, viscous liquid (94.4 g) was obtained without further purification.

The product composition was determined by gas chromatography and the results are shown in Table 1. Samples of the product mixture were observed at ambient temperature and at 0 to 5° C. for over three months and remained in liquid form.

Example 3

A Parr reactor was charged with 70.5 g (0.32 moles) phenyl-α-naphthylamine (PANA), 35.2 g acid clay F-20X (EP Engineered Clays) and 60.1 g (0.36 moles) propylene tetramer at ambient temperature. The reactor was sealed and heated with stirring to 145° C. 42.0 g (0.25 moles) propylene tetramer were added to the reactor over 3 hours at 145° C. The reaction was held at 145° C. until 80% of the PANA was converted.

The reactor was then cooled to 120° C. The pressure was released and the reactor was connected with a distillation head, condenser, receiver and vacuum/$N_2$ manifold. With stirring, vacuum was applied to the reactor and the pressure was gradually reduced to 20 torr. Unreacted propylene tetramer was removed by vacuum distillation (about 90 minutes).

Vacuum was released with $N_2$, the reactor was disconnected from the distillation column, and 46.3 grams (0.41 moles) of diisobutylene was added to the reactor. The reactor was resealed and maintained at 120° C. for 1.5 hours. An additional 14.5 g (0.13 mole) diisobutylene was added to the reactor over about 1.3 hours at a temperature between 105 and 120° C. The reaction was held at 120° C. until PANA conversion was greater than 99%.

After completion of the reaction, the acid clay was removed by filtration and the resulting filtrate was distilled under reduced pressure to remove unreacted olefins. A transparent, yellow, viscous liquid (96.1 g) was obtained without further purification.

The product composition was determined by gas chromatography and the results are shown in Table 1. Samples of the product mixture were observed at ambient temperature and at 0 to 5° C. for over three months and remained in liquid form.

Example 4

A Parr reactor was charged with 80.2 g (0.37 moles) phenyl-α-naphthylamine (PANA), 32 g acid clay F-20X (EP Engineered Clays) and 50 g (0.39 moles) propylene trimer at ambient temperature. The reactor was sealed and then heated with stirring to 145° C. 30 g (0.23 moles) propylene trimer were added to the reactor over three hours at 145° C. The reaction was held at 145° C. until 85% of the PANA was converted. The degree of conversion was monitored in situ by gas chromatography.

The reactor was then cooled to 120° C. The pressure was released and the reactor was connected with a distillation head, condenser, receiver and vacuum/$N_2$ manifold. With stirring, vacuum was applied to the reactor and the pressure was gradually reduced to 20 torr. More than 95% of unreacted propylene tetramer was removed by vacuum distillation (about 60 minutes).

Vacuum was released with $N_2$, the reactor was disconnected from the distillation column, and 25 grams (0.22 moles) of diisobutylene was added to the reactor. The reactor was resealed and maintained at 120° C. for 1.3 hours. An additional 32 g (0.28 moles) diisobutylene was added to the reactor over 1 hour at 120° C. The reaction was held at 120° C. until PANA conversion was greater than 99%. PANA conversion was determined by gas chromatography composition analysis of in-process samples taken at given intervals of time.

After completion of the reaction, the acid clay was removed by filtration and the resulting filtrate was distilled under reduced pressure to remove unreacted olefins. A transparent, yellow, viscous liquid (96.1 g) was obtained without further purification.

The product composition was determined by gas chromatography and the results are shown in Table 1. Samples of the product mixture were observed at ambient temperature and at 0 to 5° C. for over three months and remained in liquid form.

designed ratio of component of Formula I and component of Formula II in the inventive compositions.

Although the product of Comparative Example 1 is a high assay mono-alkylated PANA, it is solid at ambient temperature.

Preparation and Isolation of Mono-Nonyl PANA and Di-Nonyl PANA in High Assay

A Parr reactor was filled with 65 g (0.30 moles) phenyl α-napthylamine (PANA), 32 g acid clay F-20X and 57 g (0.45 moles) propylene trimer (nonenes). The reactor was sealed and then heated with stirring to 140 to 145° C., and 30 g (0.23 moles) propylene trimer were added over 2.5 hours. The reaction was then stopped upon completion of the propylene trimer addition. PANA conversion was 85%.

The acid clay catalyst was then removed by filtration and the resulting filtrate was distilled under reduced pressure to remove unreacted olefins, resulting in a transparent, yellow, viscous liquid product (80 g). The product composition was transferred to a 3-neck 250 ml round bottom flask attached to a Claisen head and Vigreux column. The composition was fractionally distilled under vacuum (1.5 torr) and final distillation head temperature of 235° C., resulting in 50 g material left in the pot. The composition of pot material (referred to as "Mono-nonyl PANA" in Table 2) was determined by gas chromatography and the results are shown in Table 2.

TABLE 1

| Example | wt % PANA | wt % Formula II | wt % Formula I | wt % Total di-Cn-PANA | wt % Total mono-Cn-PANA % | N wt % | Physical Form | Viscosity at 100° C. (cSt) |
|---|---|---|---|---|---|---|---|---|
| Comp1 (Irganox ® L06) | 0.1 | 99.8 | — | 0.1 | 99.8 | 4.22 | Solid | 25.5 |
| Comp2 (Naugalube ® APAN) | 7.1 | — | 89 | 4.1 | 89 | 3.75 | Liquid | 23.0 |
| Comp3 (Nonylated PANA) | 2.1 | — | 91 | 6.6 | 91 | 4.02 | Liquid | 17.7 |
| 1 | 0.48 | 39 | 59 | 1.4 | 98 | 3.84 | Liquid | 26.7 |
| 2 | 0.66 | 29 | 68 | 2.5 | 97 | 3.79 | Liquid | 27.4 |
| 3 | 0.43 | 19 | 76 | 3.5 | 95 | 3.61 | Liquid | 28.4 |
| 4 | 0.42 | 15 | 80 | 4.6 | 95 | 3.83 | Liquid | 21.0 |

As shown in Table 1, each of the product compositions of Inventive Examples 1~4 was a liquid at ambient temperature. Importantly, compared to the composition of Comparative Example 2, each of the compositions of the Inventive Examples 1-4 contained, based on the total weight of unsubstituted and substituted PANA in the composition, distinctly higher concentration of mono-alkylated PANA (at least 95% by weight) and markedly lower concentration of unsubstituted PANA (here, less than 1% by weight). Additionally, despite containing markedly lower concentrations of unsubstituted PANA, the compositions of the Inventive Examples 1 and 2 have nitrogen contents (N % by weight) similar to or exceeding the N % by weight of the composition in Comparative Example 2. This is a result of the distinctly higher concentrations of mono-alkylated PANA (and lower concentrations of di-alkylated PANA) and well- Di-nonylated PANAs was isolated by factional distillation using the same setup and similar procedure as described above. The final distillation head temperature was 270° C., and the vacuum was 1.5 torr. 22 grams of material left in the pot was obtained from a 70 gram distillation feed that contained about 13% nonene dimer, 2.7% PANA, 42% mono-nonyl PANA and 41.8% of di-nonyl PANAs and other over-nonylated PANAs in combination. The composition of pot material (referred to as "Di-nonyl PANA" in Table 2) was determined by gas chromatography and the results are shown in Table 2.

The above alkylated PANA products were formulated into Group II lubricating oil and tested for oxidation induction activity using pressure differential scanning calorimetry (PDSC) and rotating pressure vessel oxidation test (RPVOT). The results are found in the table 2 below.

TABLE 2

Antioxidative Properties of Liquid Alkylated PANA Composition

| Substance | wt % PANA | wt % Formula II | wt % Formula I | wt % Total Di-alk PANA | wt % Total Tri-alk PANA | N wt % | Viscosity at 100° C. (cSt) | PDSC (min) | RPVOT (min) |
|---|---|---|---|---|---|---|---|---|---|
| di-Nonyl PANA | <0.02 | — | 9.6 | 79.8 | 10.5 | 2.85 | 133 | 3.80 | 746 |
| Mono-nonyl PANA | 0.4 | — | 96.6 | 3.0 | 0 | 4.00 | 38 | 7.30 | 2004 |
| Comp. Example 3 in Table 1 | 2.1 | — | 91.3 | 6.6 | 0 | 4.02 | 17.7 | 6.80 | 1963 |
| Example 4 in Table 1 | 0.4 | 14.6 | 80.4 | 4.6 | 0 | 3.83 | 21.0 | 7.13 | 1970 |
| Comp. Example 2 in Table 1 | 7.1 | — | 88.8 | 4.1 | 0 | 3.75 | 23.0 | 7.13 | 1989 |
| Mono-Octyl and mono-Dodecyl PANA | 0.6 | 42.9 | 54.3 | 2.2 | 0 | 3.87 | 27.1 | 7.45 | 1977 |

At 1% weight treat rate in Group II oil, oxidation induction time measured in PDSC test indicates that di-nonyl and other over-nonylated PANA has much worse performance than mono-nonyl PANA in surface oxidation resistance. At 0.5% weight treat rate in Group II oil, oxidation induction time measured in RPVOT test indicates that di-nonyl and other over-nonylated PANA has much worse performance than mono-nonyl α-PANA in bulk oxidation resistance. Di- and other over-alkylated PANA are clearly less wanted components in alkylated PANA compositions that have commercial values. Compositions of octylated and nonylated PANA mixture, prepared in example 4, and compositions of octylated and dodecylated PANA mixture were prepared by the inventive process disclosed herein. Both compositions are stable liquid and demonstrated equivalent performance to commercial liquid alkylated PANA, e.g. Naugalube® APAN, even though the content of the more active antioxidant component PANA is lower by about 6% by weight.

Naugalube® APAN was blended with Irganox® L06 at elevated temperature and the blend was stored at 0-5° C. and ambient temperature. The ratios by weight of the Irganox® L 06 to Naugalube® APAN in the blend were 50:50 and 30:70. The initial product composition of the liquid blended product was determined by gas chromatography and the results are shown below in Table 3.

Comparative Example 4

60.6 g Naugalube® APAN (viscous liquid) and 26.0 g Irganox® L06 (crystalline powder) were charged to a glass vessel. The vessel was heated to 100° C. and held for 30 minutes under $N_2$ blanket. Heating was stopped, and the liquid sample was stirred as it reached ambient temperature. The mixture was allowed to stand at ambient temperature for eight days and observed. No visible evidence of separation was observed. A sample of the mixture was maintained at 0-5° C. and at room temperature and remained liquid over two years.

The product composition of the blended product was determined by gas chromatography and the results are shown below in Table 3 (see Comp4).

Comparative Example 5

40.0 Naugalube® APAN (viscous liquid) and 40.2 g Irganox® L06 (crystalline powder) were charged to a glass vessel. The vessel was heated to 100° C. and held for 30 minutes under $N_2$ blanket. Heating was stopped, and the liquid sample was stirred as it reached ambient temperature. The mixture was allowed to stand at room temperature. Within eight days, the mixture separated due to precipitated solid.

The product composition of the blended product was determined by gas chromatography and the results are shown below in Table 3 (see Comp5).

TABLE 3

| Example | Ingredient A | Ingredient B (Solid) | wt. ratio (B:A) | wt % PANA | wt% Total di-Cn-PANA | wt% Total Mono-Cn-PANA | Physical State (ambient temperature) | Viscosity 100° C. (cSt) |
|---|---|---|---|---|---|---|---|---|
| Irganox ® L06 | — | Comp1 (L06) | 100:0 | 0.1 | 0.1 | 99.8 | Solid | 25.5 |
| Naugalube ® APAN | Comp2 (Naugalube ® APAN) | — | 0:100 | 7.1 | 4.1 | 88.8 | Liquid | 23.0 |
| Comp4 | Comp2 (Naugalube ® APAN) | Comp1 (L06) | 30:70 | 4.5 | 3.5 | 92 | Liquid | 23.0 |
| Comp5 | Comp2 (Naugalube ® APAN) | Comp1 (L06) | 50:50 | 3.4 | 1.9 | 95 | Precipitated solid | — |

Commercial liquid product Nauaglube® APAN (Comp2) contained lower mono-Cn content, higher di-Cn content and higher PANA content. Although the blend of Comp4 produced higher mono-Cn content relative to Comp2 and stayed as a stable liquid, PANA weight percentage remained to be much higher than 1% by weight and the assay of mono-alkylated PANA was lower than 95% by weight. The blend of Comp5 produced the content of mono-alkylated PANA equal to 95% by weight; however, the mixture separated due to precipitated solid and PANA content was higher than 3% by weight.

Although particular embodiments of the present invention, including those in the particular examples above, have been described, they are not meant to be construed in a limiting sense. As will be apparent to those skilled in this art from the above specification, variations may be made without departing from the principle and scope of the present invention, which is defined by the appended claims.

What is claimed is:

1. An alkylated N-phenyl-α-naphthylamine composition comprising:
   at least 95% by weight, based on the total weight of unsubstituted and substituted N-phenyl-α-naphthylamine in the composition, of a mixture of
   (a) an isomeric mixture of mono-alkylated N-phenyl-α-naphthylamine represented by formula I

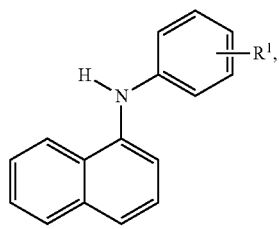

(I)

where $R^1$ represents branched alkyl derived from a mixture of alkene isomers chosen from propylene trimer, propylene tetramer and propylene pentamer, and (b) at least one mono-alkylated N-phenyl-α-naphthylamine represented by formula II

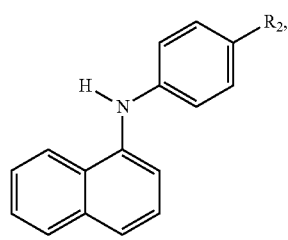

(II)

where $R^2$ is a group of formula III not derived from a mixture of alkene isomers chosen from propylene trimer, propylene tetramer and propylene pentamer, or is a group of formula IV

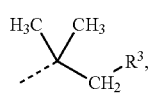

(III)

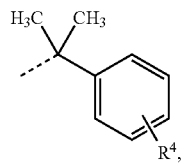

(IV)

where $R^3$ is a straight-chain or branched $C_{1-12}$ alkyl, and $R^4$ is H or a straight-chain or branched $C_{1-12}$ alkyl; and less than 1% by weight of unsubstituted N-phenyl-α-naphthylamine, based on the total weight of unsubstituted and substituted N-phenyl-α-naphthylamine in the composition, wherein the composition is a liquid at ambient temperature.

2. The alkylated N-phenyl-α-naphthylamine composition of claim 1, wherein at least 97% by weight, based on the total weight of unsubstituted and substituted N-phenyl-α-naphthylamine in the composition, is the mixture of component (a) and component (b).

3. The alkylated N-phenyl-α-naphthylamine composition of claim 1, wherein less than 0.7% by weight, based on the total weight of unsubstituted and substituted N-phenyl-α-naphthylamine in the composition, is unsubstituted N-phenyl-α-naphthylamine.

4. The alkylated N-phenyl-α-naphthylamine composition of claim 1, wherein $R^2$ is a group of formula III, and $R^3$ is chosen from $C_{1-4}$ alkyl.

5. The alkylated N-phenyl-α-naphthylamine composition of claim 4, wherein $R^3$ is chosen from t-butyl.

6. The alkylated N-phenyl-α-naphthylamine composition of claim 1, wherein $R^2$ is a group of formula IV, and $R^4$ is H.

7. The alkylated N-phenyl-α-naphthylamine composition of claim 1, wherein $R^2$ is chosen from

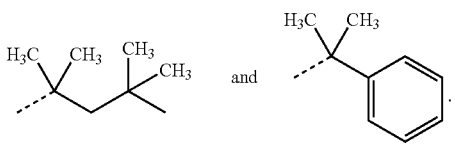

8. The alkylated N-phenyl-α-naphthylamine composition of claim 1, wherein $R^1$ in formula I represents branched alkyl derived from a mixture of alkene isomers chosen from propylene trimer and propylene tetramer.

9. The alkylated N-phenyl-α-naphthylamine composition of claim 8, wherein $R^1$ in formula I represents branched alkyl derived from propylene tetramer.

10. The alkylated N-phenyl-α-naphthylamine composition of claim 1, wherein the ratio by weight of the component (b) to the component (a) is from about 1:1 to about 0.15:1.

11. The alkylated N-phenyl-α-naphthylamine composition of claim 1, wherein $R^1$ represents branched alkyl derived from propylene tetramer, $R^2$ is chosen from t-octyl and 2-phenyl-2-propyl, and the ratio by weight of the component (b) to the component (a) is from about 0.85:1 to about 0.25:1.

12. A lubricating oil composition comprising (A) a lubricating oil and (B) an alkylated N-phenyl-α-naphthylamine composition according to claim 1 in an amount effective to provide antioxidative activity.

13. The lubricating oil composition of claim 12, wherein the alkylated N-phenyl-α-naphthylamine composition is present in the lubricating oil composition at from about 0.1 to about 10% by weight, based on the total weight of the lubricating oil composition.

14. A process for producing an alkylated N-phenyl-α-naphthylamine composition, comprising:
(i) reacting a reaction mixture comprising unsubstituted N-phenyl-α-naphthylamine, a mixture of alkene isomers chosen from propylene trimer, propylene tetramer and propylene pentamer, and an acidic alkylation catalyst to form an intermediate reaction mixture comprising an isomeric mixture of mono-alkylated N-phenyl-α-naphthylamine and residual unsubstituted N-phenyl-α-naphthylamine, and
(ii) adding at least one second olefin chosen from olefins of formulas Va, Vb and VI

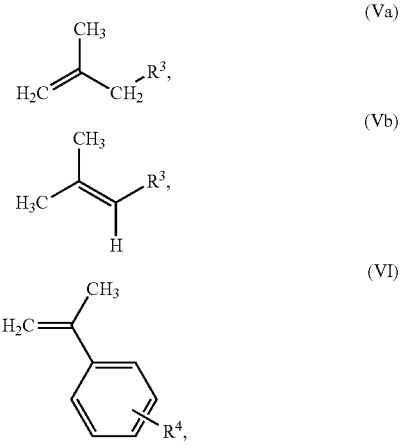

where $R^3$ is a straight-chain or branched $C_{1-12}$ alkyl, and $R^4$ is H or a straight-chain or branched $C_{1-12}$ alkyl,
to the intermediate reaction mixture and reacting the intermediate reaction mixture in the presence of an acidic alkylation catalyst to produce an alkylated N-phenyl-α-naphthylamine composition,
wherein the proportion of unsubstituted N-phenyl-α-naphthylamine in the reaction mixture that is alkylated by the mixture of alkene isomers in step (i) and the extent of residual unsubstituted N-phenyl-α-naphthylamine that is alkylated by the at least one second olefin in step (ii) are controlled such that the resulting alkylated N-phenyl-α-naphthylamine composition:
(1) contains at least 95% by weight of a mixture of mono-alkylated N-phenyl-α-naphthylamine, based on the total weight of unsubstituted and substituted N-phenyl-α-naphthylamine in the composition, and
(2) contains less than 1% by weight of unsubstituted N-phenyl-α-naphthylamine, based on the total weight of unsubstituted and substituted N-phenyl-α-naphthylamine in the composition, and
(3) is a liquid at ambient temperature.

15. The process of claim 14, wherein the resulting alkylated N-phenyl-α-naphthylamine composition contains at least 97% by weight, based on the total weight of unsubstituted and substituted N-phenyl-α-naphthylamine in the composition, of a mixture of mono-alkylated N-phenyl-α-naphthylamine.

16. The process of claim 14, wherein the resulting alkylated N-phenyl-α-naphthylamine composition contains less than 0.7% by weight, based on the total weight of unsubstituted and substituted N-phenyl-α-naphthylamine in the composition, of unsubstituted N-phenyl-α-naphthylamine.

17. The process of claim 14, wherein the at least one second olefin is chosen from olefins of the formulas Va and Vb, and $R^3$ is chosen from $C_{1-4}$ alkyl.

18. The process of claim 17, wherein $R^3$ is chosen from t-butyl.

19. The process of claim 14, wherein the at least one second olefin is an olefin of the formula VI, and $R^4$ is H.

20. The process of claim 14, wherein the at least one second olefin is chosen from diisobutylene and α-methylstyrene.

21. The process of claim 14, wherein the mixture of alkene isomers is chosen from propylene trimer and propylene tetramer.

22. The process of claim 21, wherein the mixture of alkene isomers is propylene tetramer.

23. The process of claim 14, wherein at least 40%, but no more than 80%, of the unsubstituted N-phenyl-α-naphthylamine in the reaction mixture is alkylated by the mixture of alkene isomers chosen from propylene trimer, propylene tetramer and propylene pentamer.

24. The process of claim 14, wherein in each of steps (i) and (ii) the acidic alkylation catalyst is an acid clay catalyst.

\* \* \* \* \*